US008273019B2

(12) United States Patent
Crowley et al.

(10) Patent No.: US 8,273,019 B2
(45) Date of Patent: Sep. 25, 2012

(54) CLINICAL INVESTIGATION DATA LOGGING WITH CONTEXTUAL TIME SHIFTING

(75) Inventors: Christopher Crowley, Jamaica Plain, MA (US); Stephen A. Raymond, Charlestown, MA (US)

(73) Assignee: PHT Corporation, Charlestown, MA (US)

( * ) Notice: Subject to any disclaimer, the term of this patent is extended or adjusted under 35 U.S.C. 154(b) by 482 days.

(21) Appl. No.: 12/177,540

(22) Filed: Jul. 22, 2008

(65) Prior Publication Data

US 2010/0022847 A1 Jan. 28, 2010

(51) Int. Cl.
*A61B 5/00* (2006.01)
(52) U.S. Cl. ............... 600/300; 705/2; 705/3; 368/10
(58) Field of Classification Search .......... 600/300–301, 600/500, 509, 529, 365, 485, 549; 702/127, 702/176–199; 434/322; 360/62–88, 243–247, 360/275, 327; 705/2–8, 342, 500
See application file for complete search history.

(56) References Cited

U.S. PATENT DOCUMENTS

| | | | | |
|---|---|---|---|---|
| 5,778,882 | A | | 7/1998 | Raymond et al. |
| 6,687,190 | B2 * | | 2/2004 | Momich et al. ............... 368/10 |
| 7,311,666 | B2 * | | 12/2007 | Stupp et al. .................. 600/300 |
| 7,752,059 | B2 * | | 7/2010 | Sweeney ......................... 705/3 |
| 2003/0144874 | A1 * | | 7/2003 | Barret et al. ..................... 705/2 |
| 2005/0229223 | A1 * | | 10/2005 | Katagishi et al. ............ 725/100 |
| 2006/0136267 | A1 * | | 6/2006 | Brackett et al. .................. 705/3 |
| 2007/0179361 | A1 * | | 8/2007 | Brown et al. ................. 600/300 |
| 2007/0238936 | A1 * | | 10/2007 | Becker ......................... 600/300 |

FOREIGN PATENT DOCUMENTS

WO    WO 2008001295 A2 *    1/2008

OTHER PUBLICATIONS

Cole, E. et al "A comparative study of mobile electronic data entry systems for clinical trial data collection", International Journal of Medicinal Informatics, 75 (2006), 722-729.*
Stolworthy, Y. et al "PDAS in clinical data management", SoCRA Source, Aug. 24-26, 2003.*
Guadadango, L. et al "Using PDAs for data collection", Applied Nursing Research, vol. 17, No. 4, Nov. 2004, p. 283-291.*
Koop, A. et al in "The use of handheld computers in clinical trials", Controlled Clinical Trials 23 (2002), p. 469-480.*
Missinou, M. A. et al "Short report: Piloting paperless data entry for clinical research in Africa", Am. J. Trop. Med. Hyg. 72(3), 2005, p. 301-303.*

(Continued)

*Primary Examiner* — Gregory A Morse
*Assistant Examiner* — Marie Archer
(74) *Attorney, Agent, or Firm* — Wilmer Cutler Pickering Hale and Dorr LLP

(57) ABSTRACT

A health monitoring device that includes a data logger module that collects health information from a subject or clinician during specific time ranges that are part of a health monitoring schedule. The collected health information and/or the time ranges are determined in part by the content of the collected health information. The device records the collected health information along with a time stamp. The device also includes a clock and a time shift mode that allows a user to adjust the clock to a specified point in the health monitoring schedule so that the device operates at the specified point in the same manner as if the device had reached the specified point without intervention by the user to adjust the clock.

36 Claims, 12 Drawing Sheets

OTHER PUBLICATIONS

Arzy, S. et al. "Self in time: Imagined self-location influences neural activity related to mental time travel", The Journal of Neuroscience, Jun. 18, 2008, 28(25), p. 6502-6507.*

Deser, S. et al. "Time Travel?", Extended version of the talk presented at '46 LNX 46, Cambridge, MA, 1992, p. 1-19.*
NPL_Inclinix_2005, p. 1-13.*

* cited by examiner

CLINICAL INVESTIGATION DATA LOGGING WITH CONTEXTUAL TIME SHIFTING

TECHNICAL FIELD

This invention relates to collecting and logging data from a portable device under a planned schedule. More particularly, the invention pertains to testing the portable device according to the particular schedule on the device, and training the users of the device.

BACKGROUND OF THE INVENTION

A key requirement for a valid clinical investigation is the accurate and consistent collection of subject data. Such data can include objective measurements, such as vital signs and body weight, as well as subjective patient assessments, such as a felt level of pain and emotional state. In the past, this data was gathered via paper reports (such as a "questionnaire" or a "diary"), which users (subjects and/or clinicians) would complete according to a particular schedule, often spanning a period of weeks, months, or even years. The content of each report typically consists of a series of "items" consisting of a "stem" statement, instruction, or question and structured response options pertaining to the item. Items might ask the user to enter information concerning presence and/or severity and/or duration of symptoms (e.g., nausea, headache), behaviors (e.g., took a pill, vomited, fell asleep), attitudes and emotions (e.g., anger, sadness), or other sorts of health-related information, including text or narrative.

A typical clinical investigation is planned via a "protocol" to occur as a sequence of "epochs" (often referred to as "study phases"), each specifying the treatments or activities to be undertaken during that period. Typically the collection of certain data will be scheduled to occur in one or more of these epochs such that the configuration of the data to be captured will change during the conduct of the investigation. For example, the protocol may specify that the content of a morning report change after a week has elapsed so that new questions can be posed (e.g., "Are you now taking the blue pills instead of the ones you took last week? If so, how many did you take?"). Such a change in planned content is quite common when the epoch changes. However, such changes can occur within a given epoch as well.

In order to restrict users' ability to enter their measurements and assessments to the schedule required by the clinical protocol, and to facilitate the accurate retrieval of patient data, paper reports have been replaced with electronic data loggers, often in the form of portable handheld electronic devices. An example of an electronic data logger is described in U.S. Pat. No. 5,778,882, the contents of which are incorporated herein in their entirety. Such systems only permit users to enter the required data during a time window specifically scheduled for capturing that data, which helps ensure that the data collected is valid. For example, after a subject has completed a daily data report for Monday morning, an electronic reporting device might not permit the patient to access the patient data entry screen or enter any more data for Monday, thus avoiding duplicate reports or contradicting values. Then on Tuesday morning, 24 hours after the Monday report first had become available, an opportunity for completing the new report scheduled for Tuesday morning would be made available to the subject.

There are many ways of defining a schedule for the collection of data in a clinical trial and for specifying the various conditions that need to be met in order to request and collect data. In many trials, the schedules are complex and involve conditional branching. Furthermore, trials can span long periods of time that last for many months or even years. While such complexity is helpful for enforcing conformance with the schedule for planned entry of patient data, difficulties can arise in training users in the use of electronic data logging devices that have such schedules, as well as in the development and testing of such content or the devices or systems for presenting information according to contingent scheduling.

For both training and testing, the challenge is to explore all options that can be provided by the data logging application while ensuring that the behavior of the application is not compromised in the process.

SUMMARY OF THE INVENTION

The described embodiment is an application that runs on a device for capturing, displaying, constraining, and/or storing patient data during the course of a clinical investigation. The application for the device includes a "time shift feature" that, when enabled, permits an operator to selectively skip ahead to scheduled events of interest as if that point had been reached in real time, i.e., proceeding minute by minute, day by day without jumping.

In general, in one aspect, the invention features a health monitoring device that includes a data logger module. The module is configured to collect and record a first set of health information from a user during a first time range and a second set of health information from the user during a second time range, and so on, with each time range being part of a health monitoring schedule. The second set of health information and/or the second time range may be determined in part by a content of the first set of health information. The module provides a time stamp with the recorded health information. The module also includes a clock and a time shift mode, wherein a user can adjust the clock to a specified point in the health monitoring schedule, and wherein the device operates at the specified point in the same manner as if the device had reached the specified point without intervention by the user to adjust the clock.

Various embodiments may include one or more of the following features. The health monitoring device may collect the health information in the form of diary entries. The collected health information may also include a report, a questionnaire completed by the user, or a response of the user to a medication event. The time ranges for collecting health information correspond to a specified time of day and/or a period relative to an event. When the user adjusts the clock to a specified point in the health monitoring schedule, he can do so without specifying a particular time of day. The resulting time to which the clock is adjusted relates to a time range in the health monitoring schedule during which the user is permitted to enter and/or view health information, and may correspond to the subject undergoing a medical treatment, such as taking a medication. The resulting point of time may correspond to performing a calculation based on prior health information. The health monitoring schedule may branch with the executed branches dependent upon health information received from the user.

The time shift mode of the device may be adapted in some embodiments for use in training a user of the device or for testing an application of the health monitoring device. In some embodiments, the clock adjustments involve advancing and/or retarding the clock. The user may shift to a specified point in the health monitoring schedule by specifying a time, selecting the next event in the schedule, or by selecting a point of interest. The points of interest may be defined based on whether the device is being used for training purposes or for testing purposes.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
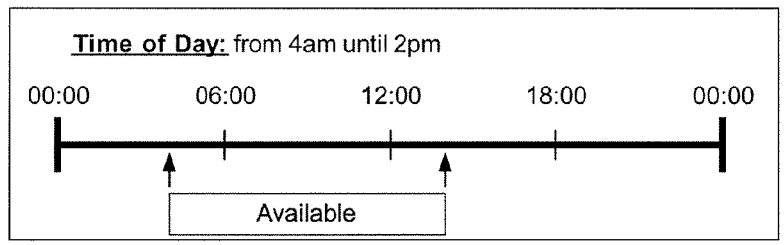
FIG. 1 is a timeline showing report availability for an absolute time of day schedule.

In general, a data logging device supports the entry of data in a prescribed fashion in applications where events and activities to be performed are scheduled according to rules. In the described embodiment, a handheld electronic device is used for entering clinical investigation data by clinicians and/or subjects. However the described methods of automating rule-based schedules are quite general, and can also be applied to areas such as automated manufacturing processes, or other methods employing heuristic logic.

This description first describes how the various types of schedules involved in the logging of data over the course of a trial are established. It then describes methods for addressing problems that arise when the described schedules are applied in typical situations, focusing specifically on the challenges of placing the device selectively, yet comprehensively, into its many possible states in a well-defined and time efficient manner.

Schedules, questionnaires, conditional branching, and other aspects of collecting data during the course of a trial are generally presented to both subject and clinician in groups in a pre-designed order as part of one or more reports. The reports are presented for completion according to a specific schedule for the entire planned period of the investigation. The schedule can involve regular intervals, such as daily between 6:00 and 11:00 am, or the schedule can be more complex, as when a clinical investigation includes several epochs. In such an investigation, each epoch may be linked to a particular purpose in the investigation design such as screening subjects, collecting baseline data, initial treatment, secondary treatment, and so on. In such cases, each epoch is associated with a particular collection of reports, with each report having a scheduled window of time for review or completion that may repeat at regular or irregular intervals. The transition from one epoch to the next can occur at a fixed, pre-specified time. More typically, however, the transition between epochs is governed by specified starting rules and ending rules. These rules depend on factors such as the completion of reports, the non-completion of reports, specific answers (responses) to certain questions (stems), time elapsed, or a combination of these.

In addition to scheduling the availability of a report for completion or review, the following are frequently scheduled as well:

1. Alarms or reminders, which may repeat, cease, and recur according to their own schedule, related to but separate from the report schedule;
2. Instructions for the subject or clinician to perform some action including the completion of reports. These instructions typically occur according to their own schedule;
3. Epochs, which themselves are internally scheduled, and for which it may be necessary to capture the timing of the changes from one epoch to the next; and
4. External events such as changes in season, time zone, daylight saving time, etc. These also can be scheduled elements that can be captured and/or be part of the scheduled operation of the application.

For the purposes of illustration, scheduled elements will be described in terms of the following parameters: base event, window of availability (described in terms of a start and a stop time), repeat interval, alarm, and triggered event, which are described next. In different embodiments, scheduled elements may include other parameters.

Report availability (availability for data entry or review on the device) can be enabled by, or based on, a variety of events, called base events. Typical events include the transition from one epoch (study phase) to another, such as from patient screening to treatment, medication events, timeout events such as the non-completion of a critical report, and the response to a particular question in a report. For example, a given report could follow different schedules depending on which epoch is active, i.e., which epoch is presently governing the rules for the operation of the logging application. Additionally, if the report were in the class of relative time reports (described below), its availability for completion would also be based on the timestamp of a triggering event that would occur during the particular active epoch.

The availability of a single report can be specified in many ways, including: always available, absolute time of day, and relative time. An always available report has no time restrictions for completion (aside from the governing epoch) in which it is available. For example, a report that records a patient's demographics would not need to be time-constrained but might be limited for initial completion only in the screening epoch, and for editing or review, only, in subsequent epochs of the same study.

An absolute time of day report has an availability window of time that is tied to the local time of day, regardless of changes in the local time due to daylight saving or shifting between time zones. For example, a report to gather a subject's quality of sleep during a preceding night might have a window of availability restricted to the period of 6:00 am to 11:00 am. This window of availability would open and closed based on local time regardless of time zone changes. So if the window opened at 6:00 am on the East Coast of the US, and the subject at 6:00 am Eastern Time flew to the West Coast, the window could be open for 8 hours rather than 5 because the time zone changed during the flight. FIG. 1 illustrates the availability for an absolute time of day schedule.

Figure 2:
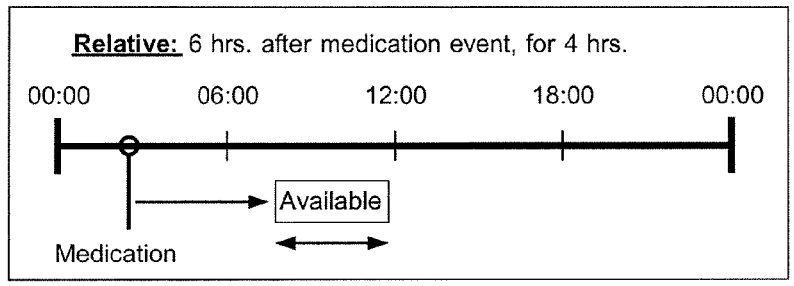
FIG. 2 is a timeline showing report availability for a relative schedule.

A relative time report has an availability window of time that is relative to a base event. Changes of time zone do not alter elapsed time and would have no effect on either the duration of time between the triggering event and the report availability, or on the duration of the window of availability. For example, consider a report that records a patient's pain level an hour after receiving medication. This interval of an hour would be honored regardless of any change in the local time due to a change of time zone or a change from standard time to daylight saving time. FIG. 2 shows a relative time schedule for availability of a single report. In the illustrated case, the delay before report availability is fixed at 6 hours from the timestamp of a medication event. Since medication events can occur at any time of day, and trials are usually interested in the effect of the medication at various times that have elapsed since the subject takes the medication, the report availability is set in terms of relative time and not in terms of a fixed time of day.

Figure 3:
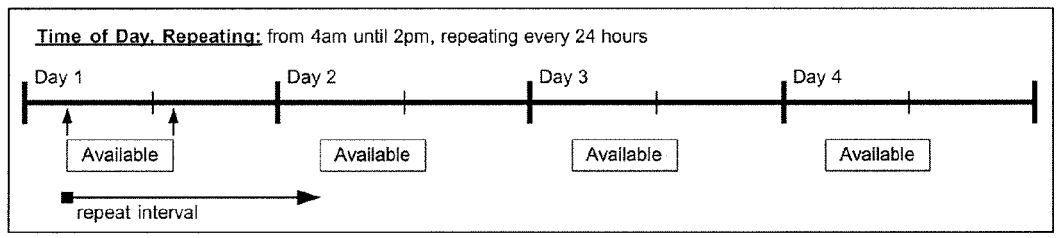
FIG. 3 is a timeline showing report availability of a repeating schedule.
Figure 4:
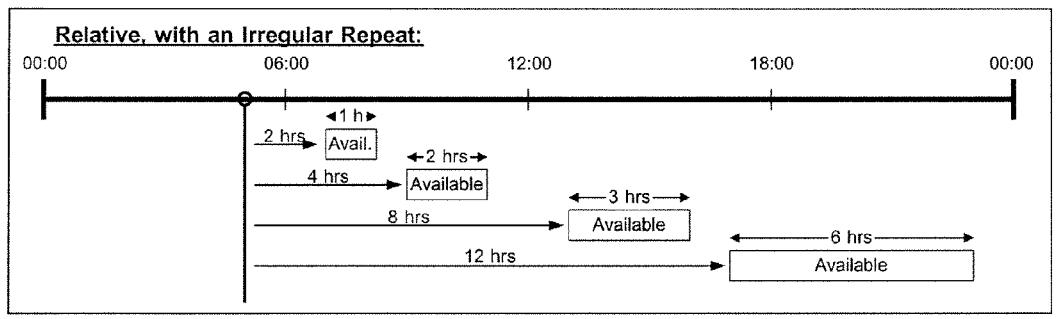
FIG. 4 is a timeline showing report availability for a relative, irregularly repeating schedule.

In many cases, availability of a report of a specific type will be followed by additional instances of the availability of reports with the same item content. This repetition can be classified as a regular repeat or an irregular repeat. The availability of regularly repeated reports recurs after a fixed interval or regularly at the same times on successive days. If applicable, the timing is adjusted for changes in time zone (e.g., with shift) or changes in local time from standard to daylight saving time. For example, a report to gather a patient's quality of life or presence of symptoms might be made available within the same window of time every day regardless of when, in that same window of time but on a previous day, a previous report had been completed. FIG. 3 shows an example of a schedule that is available on a regular, time-of-day repeat cycle. By contrast, the availability of irregularly repeated reports recurs after specific but varying intervals of time. The duration of the window of availability can also vary. For example, a first set of reports to gather changes to a subject's pain level after receiving medication might initially repeat after short intervals, but at a later time both the interval and duration of availability for report completion might increase in order to reduce the burden on the subject. For example, availability of such a report might first occur 15 minutes after a medication event and persist for only 5 minutes, then repeat at 30 minutes after the event for a duration of 10 minutes, then at one hour for 15 minutes, at three hours for 30 minutes, etc. Another example of irregularly repeating report availability is shown in FIG. 4. This illustrates how a complex, irregular repeating schedule of windows of availability can be defined by combining multiple single-event schedules; each of four windows of availability is defined with an individual schedule using a relative availability window based on the same base event.

Figure 5:
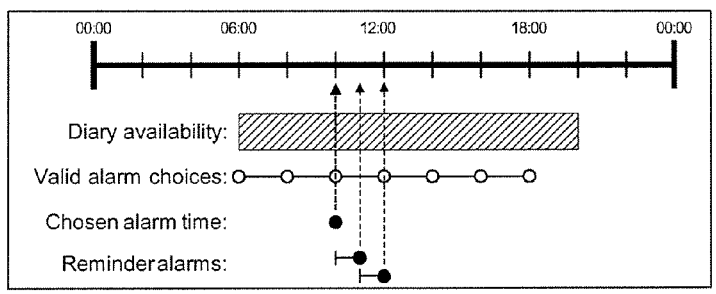
FIG. 5 is a timeline showing an alarm schedule.

For a given investigation, each device has a program that schedules report availability as well as other elements of the investigation. These additional schedules can specify a string of notification alarms, each with follow-up reminder alarms. For example, an evening report available between 5:00 pm and 11:00 pm can be heralded by having the device sound an initial alarm at 5:00 pm to announce the beginning of a period of availability for completion, and then sound again at each of the next three half-hour marks, or for the duration of the report availability, to repeatedly remind the subject to complete the report until the report is completed or the window of availability closes. These alarms and reminders can be considered as attributes of the reports themselves, and can be variously scheduled. FIG. 5 illustrates an alarm event schedule with its own determined sequence of timings within the window of the report availability. An alarm event can be set to trigger additional reminder alarms, which would be set to occur at yet another interval until the report (or event in general) was completed.

Figure 6:
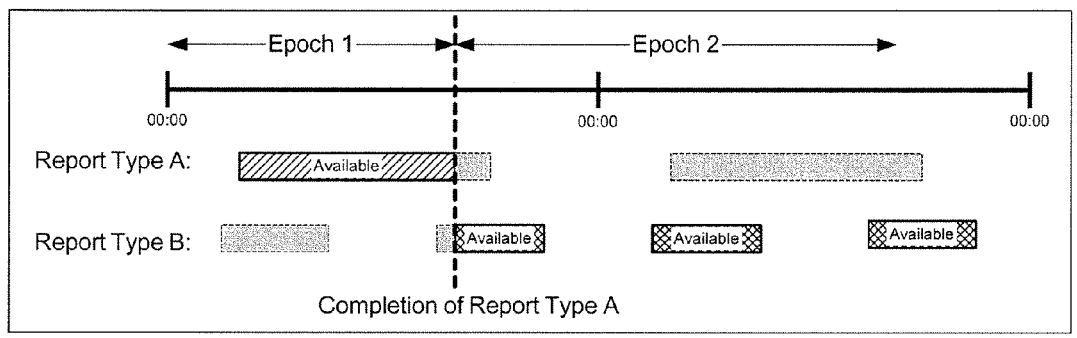
FIG. 6 is a timeline showing epoch change based on report completion.

Upon the completion of a report, a new base event can occur, and trigger a transition from one epoch to another. For example, completion of a first study medication report can trigger a new epoch of the investigation. For clinical trials, this often corresponds to the transition of the subject from a screening epoch to a treatment epoch. The new active epoch is a state parameter that can be set to enable a new set of reports. The base event timestamp itself could now become the origin or reference for any relative reports. FIG. 6 illustrates an example of an epoch change tied to the completion of a particular report. In this example, Report Type A repeats daily and is available until it is completed once. Report Type B repeats every 12 hours but is only available in Epoch 2, which begins after the single completion of Report Type A. Thus, initially Report Type B is not available but Report Type A is. Once Report Type A is completed, which could be at any time during its availability, the device changes state to Epoch 2. Now, Report Type A is no longer available as it has been completed the requisite single time, and Report Type B is now available as the device has now entered Epoch 2. This example typifies the sort of scheduled report availability preceding and following a medication event, after which a series of reports might need to be completed to assess the effects of the medication over time.

Figure 7:
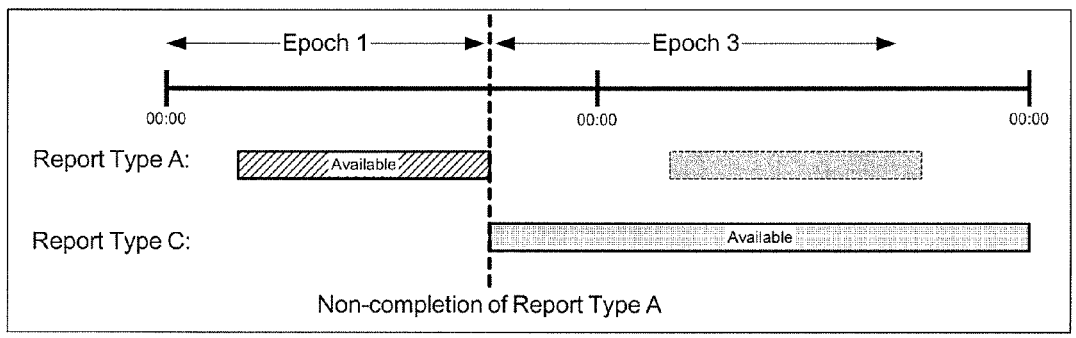
FIG. 7 is a timeline showing epoch change based on report non-completion.

FIG. 7 illustrates an example of an epoch change tied to non-completion of a report. It is similar to the previous example in FIG. 6 and could occur with the same schedule except in this case an epoch change is triggered by a different activity, namely Report Type A not being completed. Once the availability window for Report Type A closes without completion, the device switches immediately to Epoch 3, thus causing the scheduling engine to activate a different sequence of events for the device, represented in this example as a new Report Type C becoming available as shown in FIG. 7. An important difference from the prior case where user activity (Report Type A completion) triggered the epoch change is that in this example of non-completion, the device must make this transition without human intervention. This example typifies the sort of schedule of report availability where a "washout" epoch must occur if a subject does not unambiguously confirm medication consumption.

Figure 8:
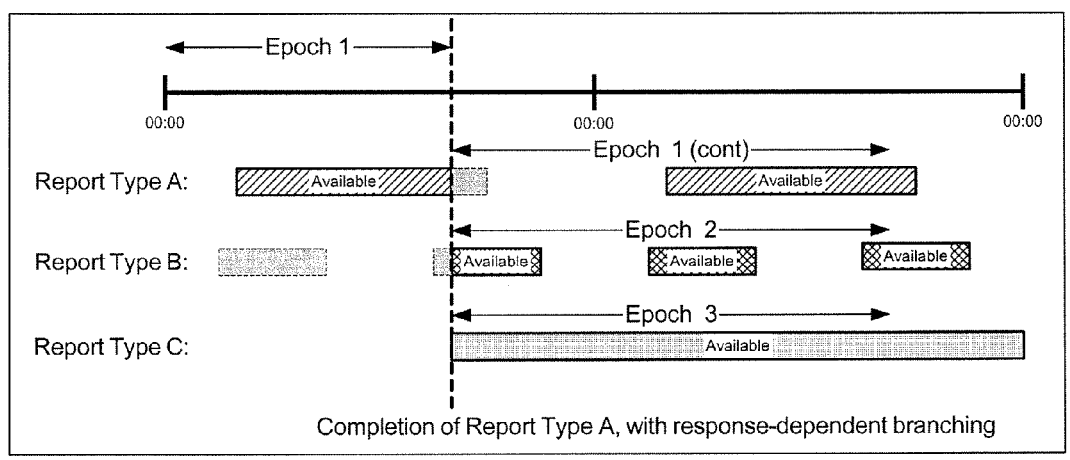
FIG. 8 is a timeline showing epoch change based on data in a report.

FIG. 8 illustrates an example of an epoch change dependent on the data contained within a report. It shows a third type of epoch branching whereby the decision of which epoch, if any, to branch to depends upon specific responses to items within Report Type A. In the illustration, depending on how the user responds to questions in Report Type A, the device may transition to one of several possible epochs or may continue to remain in Epoch 1.

Figure 9:
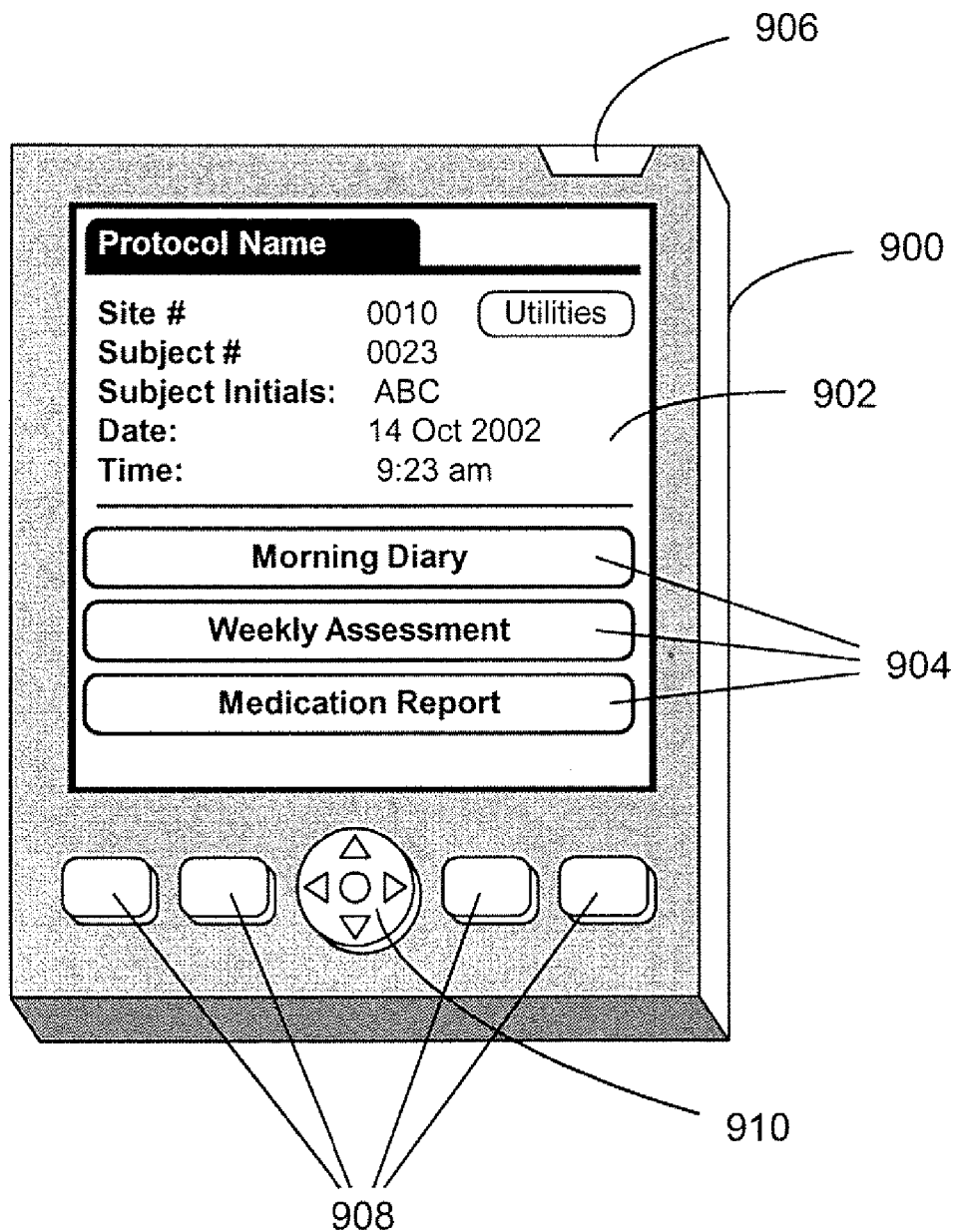
FIG. 9 is an illustration of a data logging device.

In the described embodiment, clinical data logging is performed using a portable electronic device. FIG. 9 illustrates such a device (900), showing display area 902, patient input area 904 (consisting of both a display and a touch-sensitive overlay), power switch 906, optional stylus (not shown), hard keys 908, navigation input device 910, internal battery (either replaceable or rechargeable, not shown), and one or more of the following internal or external components (not shown): modem, wireless transmitter, cellular transmitter, infrared transmitter, network connection.

Figure 10:
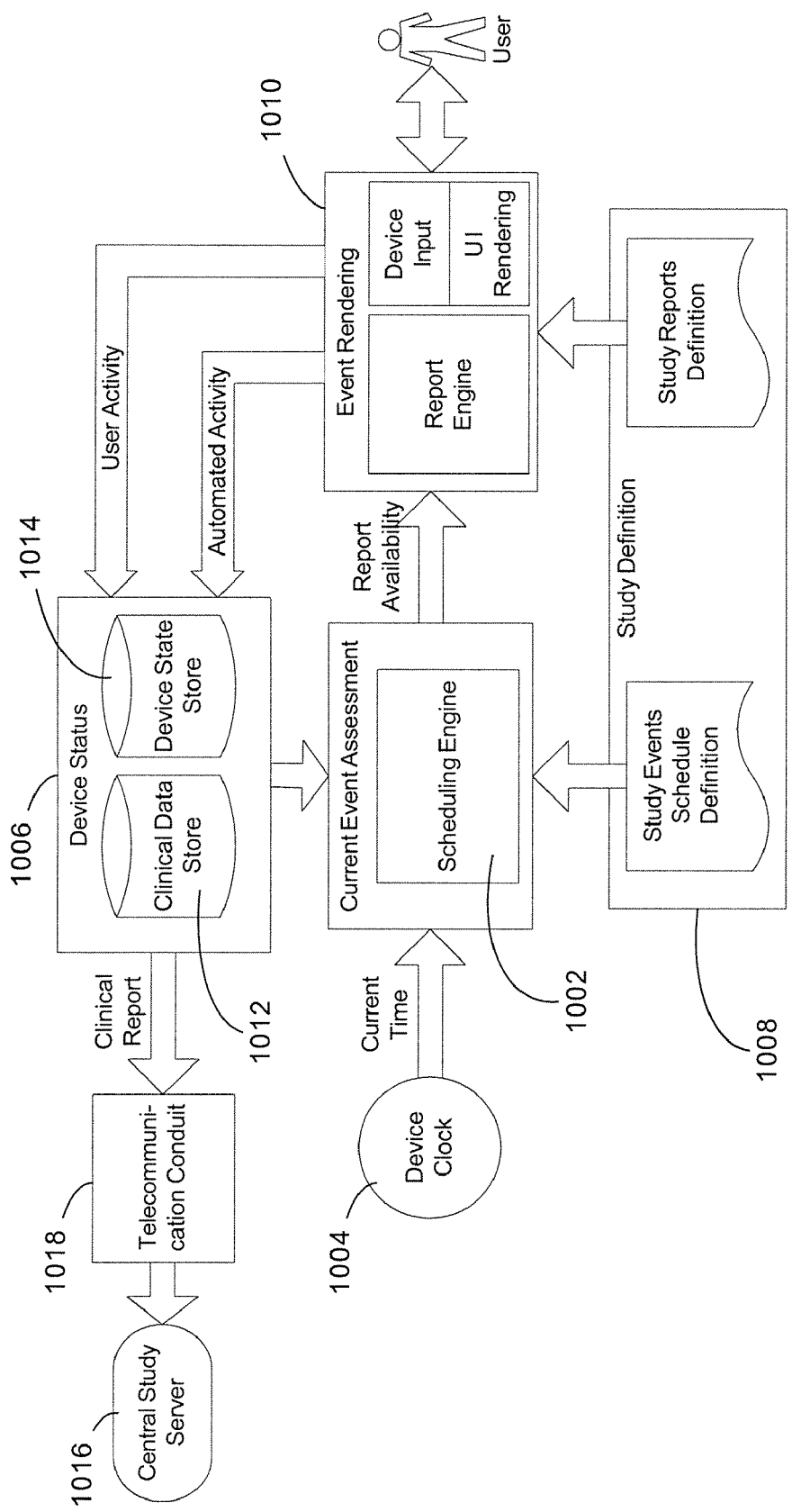
FIG. 10 is a simplified block diagram of a clinical data logging application.

FIG. 10 is a simplified block diagram of a clinical data logging application that runs on device 900. As depicted, scheduling engine 1002 determines which conditional or scheduled events are currently active or available for action, for example which reports are available to the user for completion. This determination is based upon device clock 1004, device current status 1006, and the specific study definition 1008 that is being used. When the scheduling engine determines an event is active according to study definition 1008, whether by direct user interaction or on a purely automated basis, the event rendering module 1010 carries out the appropriate device changes. For example, when a report becomes available, the data logging application will indicate its availability by displaying a button on display 902, and optionally with an alert tone. Once the user indicates a desire to complete the report, event rendering module 1010 manages the display of each item and the retrieval of the user's response for each item based on the specific study definition 1008. When complete, the user's responses are stored in clinical data store 1012 along with additional non-clinical supporting information such as timestamps, time zone, and device status, that are stored in device state store 1014. This additional information is useful for monitoring and maintenance of the device, and helps ensure that the device is working properly. As a final step, collected data is transmitted to centralized server 1016 via telecommunication conduit 1018, such as via a modem, TCP/IP Network, or cellular wireless network using a variety of connection means such as a phone line, network connection, Wi-Fi, infrared, Bluetooth, and cellular transmitter.

Figure 11:
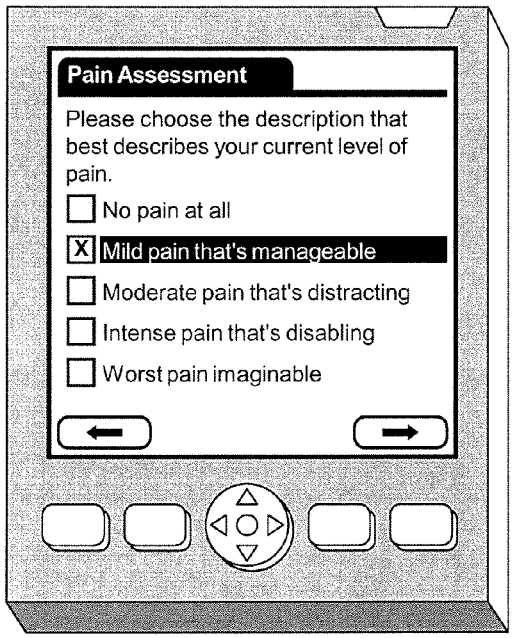
FIG. 11 is an illustration of a data logging device displaying a subject report.

In FIG. 9, display 902 shows a "gateway" screen from which a user may begin a report. In FIG. 9, three reports are shown: Morning Diary, Weekly Assessment, and Medication Report. Typically, a report would only be visible if it were available for the user's immediate use. FIG. 11 shows an example of an item in a report to be completed by a patient participating in a clinical investigation. A user may respond to any particular item in a report through a multitude of data entry methods. Common modalities include, but are not limited to: number spinners, in which a user selects numerical values by "spinning" virtual number wheels; date pickers, in which a user selects a date from a calendar; time spinners, in which a user selects a time by spinning a virtual digital clock; visual analog scale (VAS), in which a user inputs a value with virtual sliders or dials; free text entry; and drop lists that contain a list of the permitted replies. The subject enters or selects responses in patient input area 904. The availability of each report, and therefore the possibility of responding to it, is restricted to the specific schedule of the clinical investigation involved. Examples of clinical investigation schedules are described below.

Scheduling engine 1002 provides a customizable means of controlling the schedule for each clinical study that is to be implemented in the application on handheld device 900. The scheduling engine enables a programmer to specify all the key aspects of the schedule. Such aspects include but are not limited to: windows of time during which actions, such as collection of patient data, can occur; execution of calculations to be performed on data; and triggering of reminder alarms. Reminder alarms serve to remind users when to complete a report, when to take a medication, when to perform a task such as measuring their body temperature and blood pressure, or when to appear for their next clinical visit. Each of the aspects that are programmed into the system become manifest at some point during the clinical investigation schedule if the appropriate conditions are met. For example, device 900 reminds subjects to perform data entry or to perform an action (such as take a pill), and then allows them to enter data in response to the items in a questionnaire or in a diary. Subjects can also document that a scheduled action has occurred or the device could track and report on a subject's level of compliance with scheduled tasks such as report completion or medication consumption.

Figure 12:
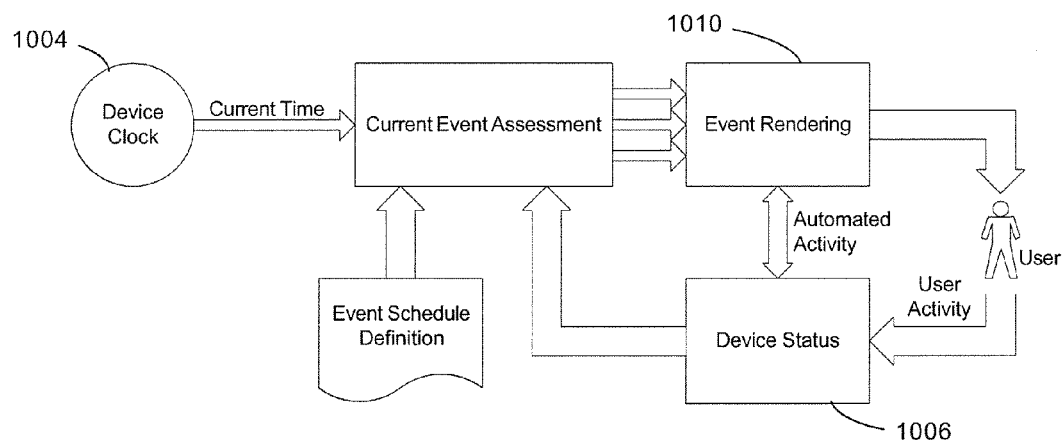
FIG. 12 is a flow diagram of activities performed by the scheduling engine.

FIG. 12 is a simplification of FIG. 10, emphasizing the functions central to the discussion of the described embodiment. The scheduling engine is driven by device clock 1004. Using the time received from the device clock, the scheduling engine evaluates the device's current status against the particular schedule definitions for the study in question. The scheduling engine then determines which scheduled application behaviors are currently active (such as an assessment epoch), available (such as completing a specific report), or are expected to occur (such as a reminder alarm if the report is not completed in time). As shown in FIG. 12, this process of evaluation is referred to as "Current Event Assessment." In the figure, "Event Rendering" 1010 refers to the means for effectuating an event on the device through a variety of channels, such as by changing the visual display, by sounding audible alerts, or by causing internal state changes. The path in the diagram from "Event Rendering" through "User Activity" and "Device Status" 1006 shows that user activity or automated processes can lead to changes in the device's state and thus affect the ongoing scheduling operations of the device as an input to the Current Event Assessment process.

Figure 13:
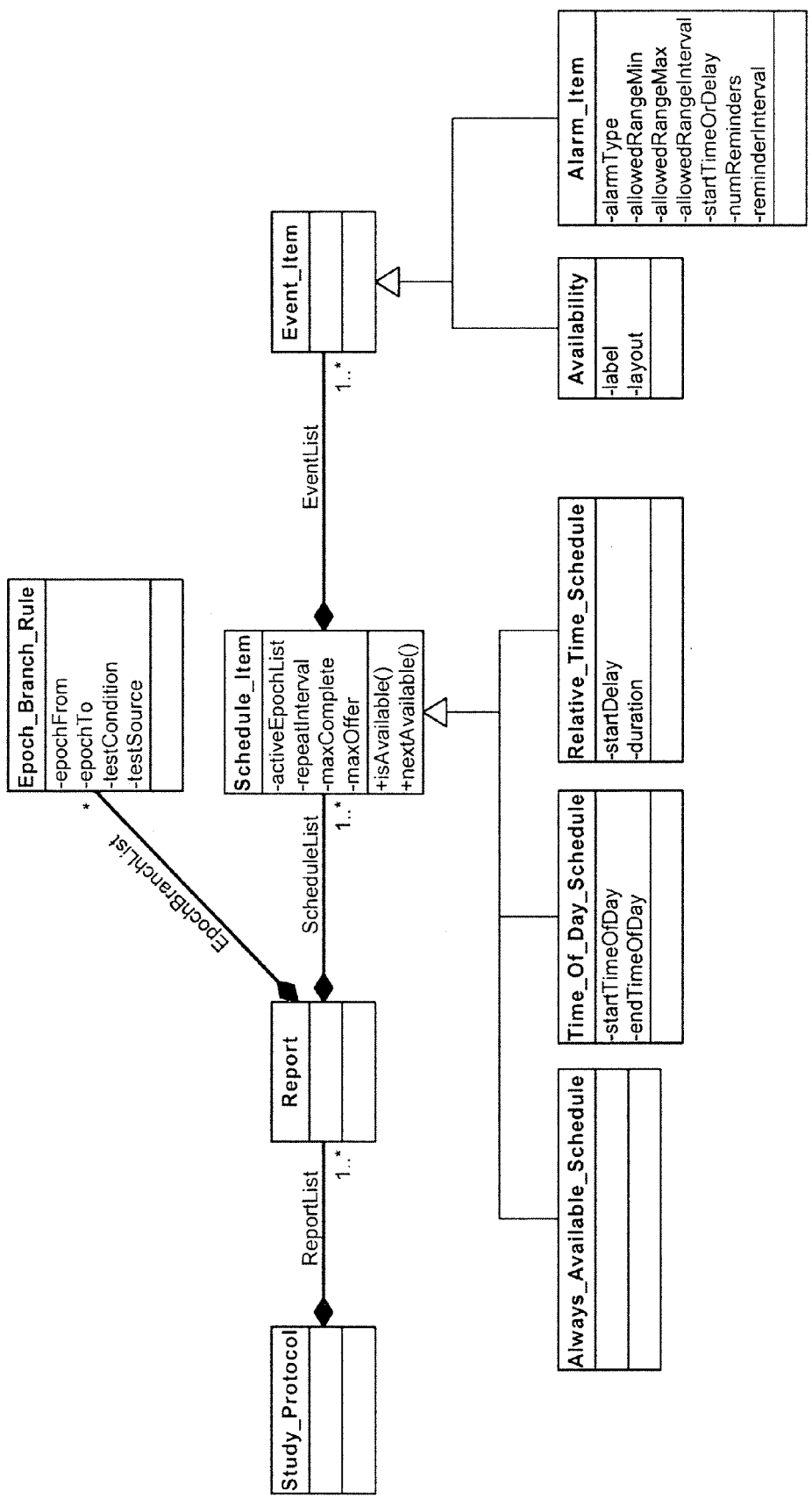
FIG. 13 is a UML description of a study protocol using the report scheduling scheme of the described embodiment.

FIG. 13 is a Unified Modeling Language (UML) diagram describing a given study protocol using the report scheduling scheme described above. The figure shows that a given study protocol contains one or more reports, with each report in turn having at least one "Schedule Item" element to determine the availability of that report according to a set of rules or "Schedule." Regardless of the type of schedule, all schedule items in this example will have a list of the epochs (phases) to which the schedule pertains, a repeat interval in the case of a regular repeating item, and maximum limits for the number of times the report will be offered and/or may be completed. In addition to these common elements, "Time of Day" and "Relative" schedule types require additional information to define a window of availability. For example the "Time of Day" schedule type may have variables specifying starting and ending times, whereas a "Relative Time" schedule type may have variables giving the initial delay from the base event and then the duration of the availability window.

Schedule items are used to specify a period of activity for reports or other events; event items are used to specify the type of activity that should occur. Each schedule definition includes one or more elements specifying the occurrence of events such as the availability of the report or an alarm. For an alarm, the Event Item includes the type of alarm (e.g., sound, vibrate, and/or visual), time of day or delay from a triggering event for the first alarm (depending on the schedule type), the number of any follow-up reminder alarms and interval of time before each one occurs. Frequently, the user of the device is enabled to select an initial alarm time from a range of times. This range is defined by the minimum, maximum, and possibly a step size that defines the valid choices in between (e.g., from 9:00 am to 11:00 am on the whole hours only).

The final element that is used to configure a schedule is a list of relevant epochs and definitions of "Epoch Branching Rules" for how and when to transition between them. While a given study protocol can have many methods of changing epochs, such changes are typically associated with the completion of a report. For this reason the branching rules are shown in FIG. 13 as "aggregate" objects owned by or attributed to the report, where each report may have any number of branching rules to be evaluated upon the completion of the report. Each rule includes the epoch in which the rule should be evaluated (called the "From" epoch), the epoch to which the device will transition if the rule evaluates as true (called the "To" epoch), and the test to be evaluated, consisting of a data source and a condition (algorithm) to be applied to the data source. For example, a device might transition from a screening epoch to a treatment epoch if a particular report indicates that the subject has been given a medication or procedure.

Time Shift Feature

The above discussion of scheduling of the availability of reports and occurrence of events introduces the context and definitions to reveal how the invention solves an important problem for devices that operate according to rule-based schedules. Having described various ways of scheduling the availability of reports and occurrence of event schedules for the data logging device, the following description now addresses the challenge referred to above concerning the training of clinicians and subjects in the use of the data logging device, as well as in developing and testing the data logging application that runs on the clinical data logging device. As previously mentioned, the challenge concerns placing the device into each of its many possible states in a time efficient manner such that the device behaves in the same way that it would if it had reached that state in real time.

As discussed above, clinical investigations often extend over a period of weeks and months, and sometimes even over years. A key feature of handheld device 900 is that it follows the precise sequence of actions specified by the clinical investigation. But this raises a difficulty for training and testing because it is not practical to wait for the time intervals involved in the investigation to reach all the actions that must be understood by users and tested by developers. In order to address this problem, the described embodiment implements a "time shift" feature that can be activated for training and testing purposes. This feature allows the device user to manipulate the clock to jump ahead in time, while otherwise allowing the device to operate exactly as it would in real time. When time shift is activated, the logging of data also operates just as it does in real time, thus accumulating a realistic history of timed reports, such as daily diaries. In the described embodiment, the time shift feature is exercised by advancing the clock into the future. If it is desired to restart the schedule at an earlier time, or to retard the clock, the device state corresponding to the earlier time must be restored and intervening data and reports deleted. A method for accomplishing this is presented below.

In the described embodiment, the time shift feature is keyed to schedule events (Schedule Items) that have been programmed into the application. This enables scheduling engine 1002 in the device to determine at what time the next event of interest occurs and to automatically advance the device clock 1004 to just before that time. Such automated time jumping avoids the burden of manually calculating when the next action of interest occurs, and then manually changing the clock to reveal or enable that action.

Figure 14:
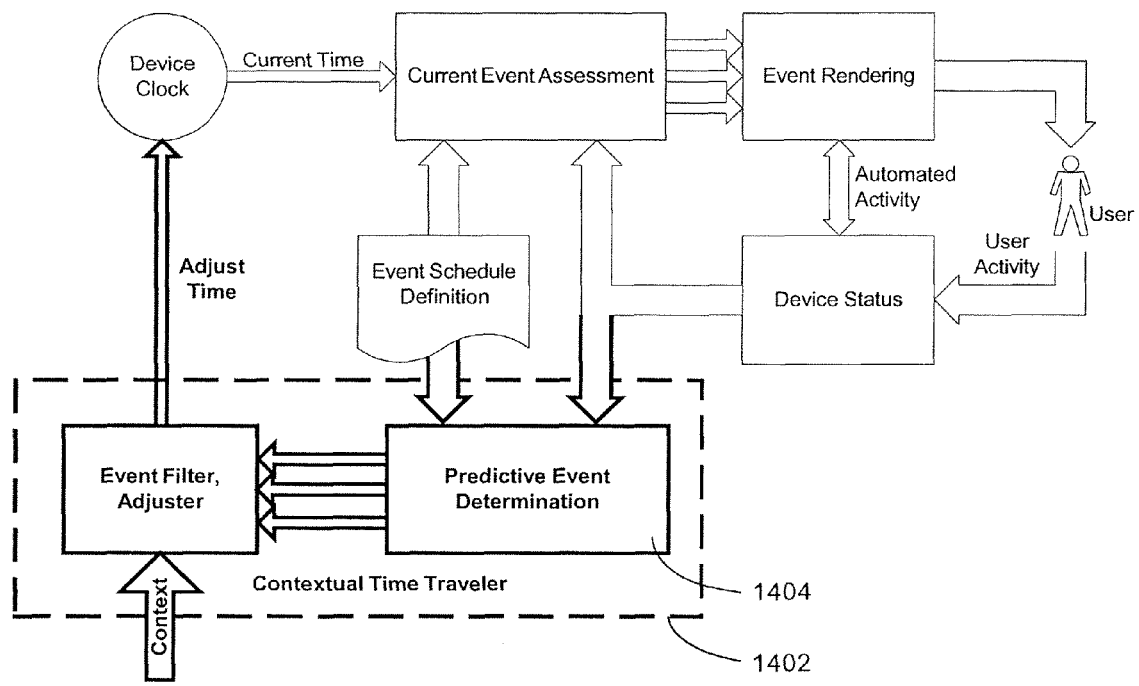
FIG. 14 is a functional block diagram of the data logging application illustrating the time shift feature.

FIG. 14 is a functional block diagram illustrating the time shift feature and its relationship to the other elements of the software application running on device 900. The event scheduler, described above and shown in FIG. 12, is augmented by contextual time shifter 1402, which includes the function labeled "Predictive Event Determination" 1404. This function relies on the same scheduling definitions that are used to define how windows of availability and events are set up by the main scheduler. Therefore the predictive event determination process can read (consume) the scheduling rules and event schedule definitions to determine when subsequent events will occur given the current status of the system. The output of predictive event determination 1404 is a list of potentially "interesting" events such as report availability, alarm sounding, or epoch changes due to passage of time.

From this list of events, the truly "interesting" ones are selected, based on the device context and/or user configuration. For example, in a training context, the availability of reports and the operational effects of epoch changes would be of most interest, whereas in a testing context the events of interest might be the moments just before report availability and expiration, the moment just before an automated phase transition, and the moments just before an alarm and each of its associated reminders. From this list of filtered events, the application then selects the next one to occur, based on the type of time shifter selected by the user (see below), and sets the system clock to an appropriate time to enable the activity or event.

The time shift feature achieves its purpose by changing the device clock without affecting any of the in situ scheduling or behavioral functionality. By changing the scheduled behavior in this manner, one can be assured that the situations encountered during training and in the results of product testing will apply to the device as operations unfold in real time. This helps ensure that users receive a comprehensive training and that the product behaves reliably and predictably.

Figure 15:
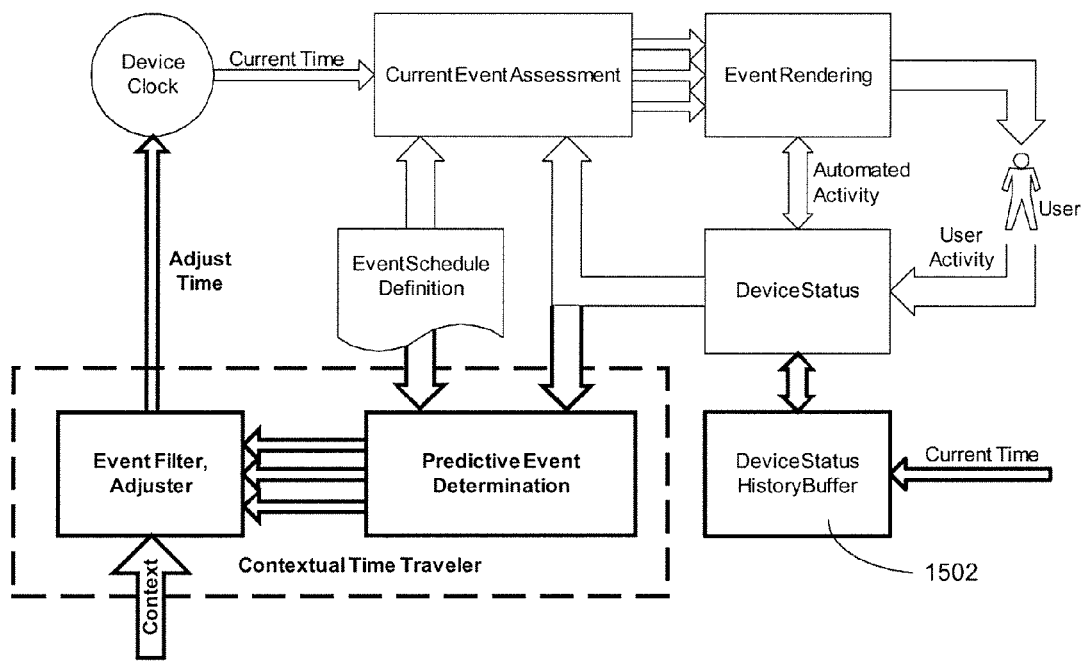
FIG. 15 is a functional block diagram of the data logging application including a history status buffer.

The device can be implemented in such a way as to support jumping back in time as well as forward. For forward only movement, as described above, the system only needs to maintain its current state. To jump backward or retard the clock, the system needs to maintain a state history, for example by using device status history buffer 1502 as shown in FIG. 15. With this configuration, the history buffer would either store or be able to determine the device status for any past or current point in time. When the device clock is set back in time, the buffer provides this older status information to the predictor. In certain implementations, reverting to a past time erases all status information after a past point in time where a status change is made.

Example Implementation of Algorithm

Having discussed the functional components of the time shift feature, we now will show slightly more detail in a "pseudo-code" style with a simple implementation of the feature. In this example we are only choosing the very next moment "of interest" that would naturally occur, and to which the device's clock will be set. This is accomplished by a function such as findNextJumpPoint, below, which will determine the earliest point in time from all the start times of all scheduled windows of availability, and the possible expiration time of the current epoch:

```
/*
 * Simple function for determining the single, next event of
 * interest to occur, where only the start of availability and
 * epoch expirations are considered.
 */
function DateTime findNextJumpPoint( ) {
    DateTime jumpPoint = null;
    foreach Schedule in ScheduleList {
        Next = findNextStart(Schedule);
        if (Next != null) {
            if (jumpPoint == null || Next.start < jumpPoint) {
                jumpPoint = Next.start;
            }
        }
    }
    if (CurrentEpoch.timeout < jumpPoint) {
        jumpPoint = CurrentEpoch.timeout;
    }
    return jumpPoint;
}
```

A possible means of determining the next start time for any particular scheduled window of availability, is shown below in the function findNextWindow. The technique here is to first determine whether the schedule in question is even active or "interesting". Then, determine its first occurrence (past or future) in the current epoch, according to the schedule's definition and the base time event of the current epoch. Finally, determine whether or not the schedule repeats, and based on that, which iteration (including the $0^{th}$) will next occur (if at all).

```
/*
 * Determines the next window of availability to occur for a given
 * Schedule item. The item is only considered if it is "of interest"
 * and currently active, including but not limited to consideration of
 * whether any repeat or completion limit has been reached.
 */
function Window findNextWindow(Schedule) {
    Window NextWindow = null;
    if (Schedule.isActive(CurrentEpoch)
            && TimeJumper.isInteresting(Schedule, Context)) {
        DateTime now  = getCurrentDateTime( );
        DateTime base = CurrentEpoch.start;
        Window First  = findFirstWindow(Schedule, base);
        int    iteration = findNextIteration(now, First, Schedule);
        if (iteration >= 0) {
            DateTime start   = (First.start
                              + iteration * Schedule.repeatInterval);
            DateTime end     = (First.end
                              + iteration * Schedule.repeatInterval);
            if (start > now) {
                NextWindow.set(start, end);
            }
        }
    }
    return NextWindow;
}
```

The first occurrence of a schedule's window of availability can be determined with a function such as findFirstWindow, below:

```
/*
 * Determines the first window of availability to occur (or have
 * already occurred) for a given Schedule item.
 *
 * Not shown is consideration for whether the first window is allowed
 * to "straddle" the base time. That is, if a virtual start time
 * before the base time would have a corresponding end time after the
 * base time, thus effectively making the first window "already in
 * progress" as the epoch began. This is useful for daily reports
 * (e.g.) that repeat across epoch changes.
 */
function Window findFirstWindow(Schedule, base) {
    Window First = null;
    if (Schedule.isRelative) {
        First.start = base + Schedule.delay;
        First.end   = Fist.start + Schedule.duration;
    } else if (Schedule.isTimeOfDay) {
        baseAtMidnight = DateOnly(base);
        First.start = baseAtMidnight + Schedule.startTimeOfDay;
        First.end   = baseAtMidnight + Schedule.endTimeOfDay;
        // it is assumed Schedule.startTimeOfDay and .endTimeOfDay
        // include days of initial delay and additional duration,
        // respectively, as necessary.
    }
    return First;
}
```

And the iteration of the next window of availability can be determined with a function such as findNextIteration, below:

```
/*
 * Determines which iteration is next to occur given the current time,
 * the first window of availability, and the repeat interval.
 * The first window is considered iteration 0.  -1 indicates there
 * is no next iteration.
 */
function int findNextIteration(now, First, Schedule) {
    int iteration = -1;
    // for repeating reports
    if (Schedule.repeatInterval != 0) {
        iteration = floor((now - First.start) / Schedule.repeatInterval);
    // for non-repeating reports
    } else if (First.start > now) {
        iteration = 0;
    }
    return iteration;
}
```

The above methods and algorithms show only one of many possible implementations and ignore or abbreviate the proper handling of a number of possible variations and situations. For example, as briefly mentioned, it may be desirable to let a report "straddle" an epoch. That is, to permit an availability window that would have started before the epoch began but extended into the epoch's activity. This behavior would allow a report's repeating window of availability to continue uninterrupted (in appearance) across an epoch change. There is also the issue of report overlap or "stacking" where a report's availability duration is longer than its repeat interval. In this situation, a report can "stack up" if not completed immediately, with the result that multiple iterations can be available concurrently. The actual handling of this availability may vary from one implementation to the next, and can be further complicated when combined with the "straddling" behavior.

Example Implementation of User Interface

Figure 16:
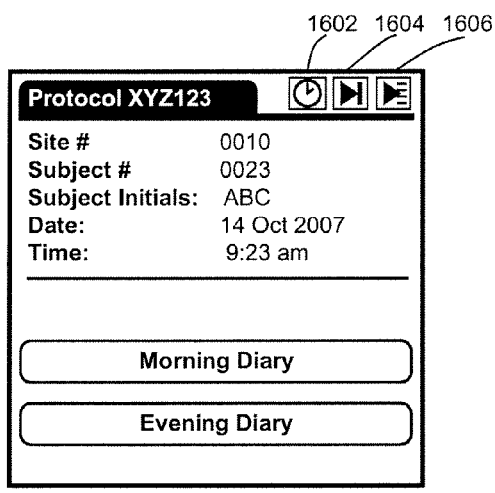
FIG. 16 is a screen display showing time shift control icons.

FIGS. 16-19 illustrate a user interface for controlling the time shift feature. The figures show screenshots of touch-screen devices that can be tapped by a user to engage the time shift feature. The described embodiment includes three time shift modes: jump ahead to a specific time; jump ahead to the next event; and jump ahead to a selected event of interest. In FIG. 16, each of icons 1602, 1604, and 1606 at the top right of the screen represent one of the three time shift modes, which, when touched, triggers one of the three methods of time jumping.

Figure 17:
FIG. 17 illustrates a user interface for the specific time mode of time shift.
Figure 17:
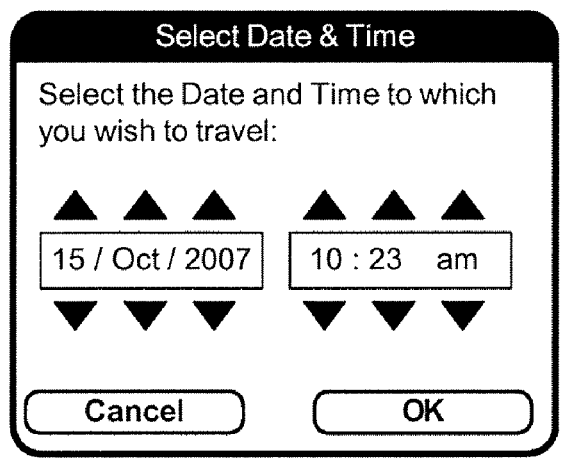

FIG. 17 shows an implementation of the time shift mode whereby a user jumps ahead to a specific time, activated by tapping on icon 1602, in which the user is presented with a date-time spinner. The range of the spinner can be constrained within minimum and maximum boundaries. While this option for controlling the device clock allows the user full freedom of selection, it does not provide information about the qualitative importance of any particular point in time in relation to the specified schedule. A user must know the schedule in order to jump to the times that exercise the scheduler and reveal the time-dependent operation of the application.

Figure 18:
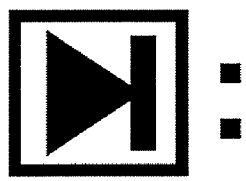
FIG. 18 illustrates a user interface for jumping ahead to the next event mode of time shift.
Figure 18:
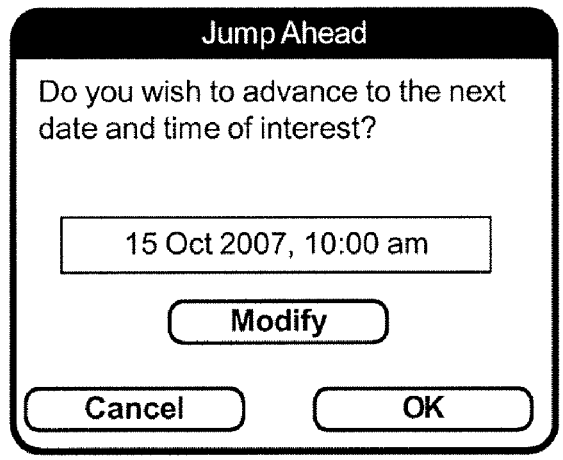

A second option, activated by tapping on icon 1604, is shown in FIG. 18 and takes advantage of the system's schedule and event definitions to allow the user to advance the time to reveal the next scheduled activity or event. This depends on the various scheduling variables, state of the device, and currently active epoch. By default the dialog shown on the screen displays the next moment of time automatically determined by the system to be "interesting" based on predictive event determination 1404 as part of the contextual time shifter feature. The user could simply accept this default (by tapping OK) or could modify the time via a dialog such as that shown in FIG. 17. As described above, the predictor would use the device's current use context (e.g., training, testing, etc.) to select, adjust, and present the next moment typically of interest, thus allowing the user to quickly move through the clinical protocol's scheduled activity.

Figure 19:
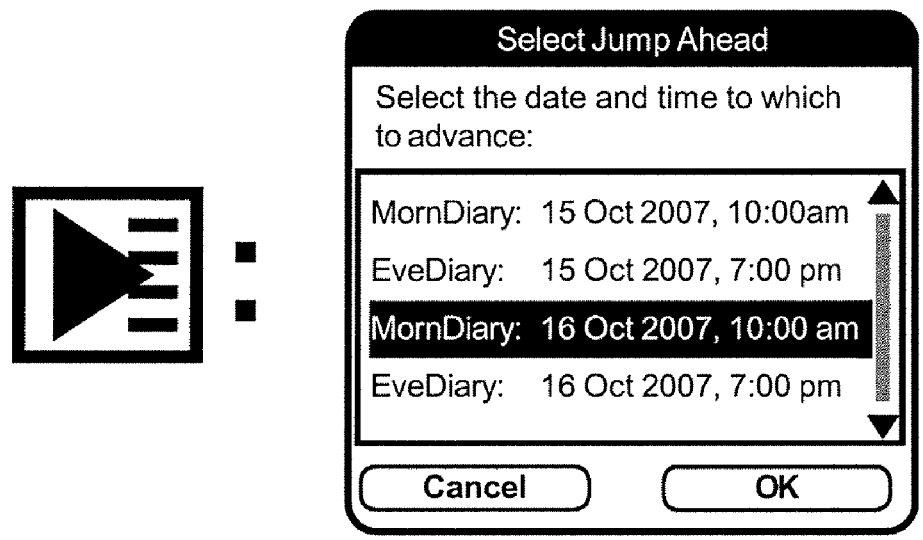
FIG. 19 illustrates a user interface for jumping to the next event of interest mode of time shift.

FIG. 19 shows an implementation of the third mode of time shift, activated by tapping on icon 1606, which is an extension of the second mode. In this mode, the system determines a list of events from which to select, while also indicating the nature of the event. This provides the speed, convenience and informed context of the second approach with some additional flexibility.

Figure 20:
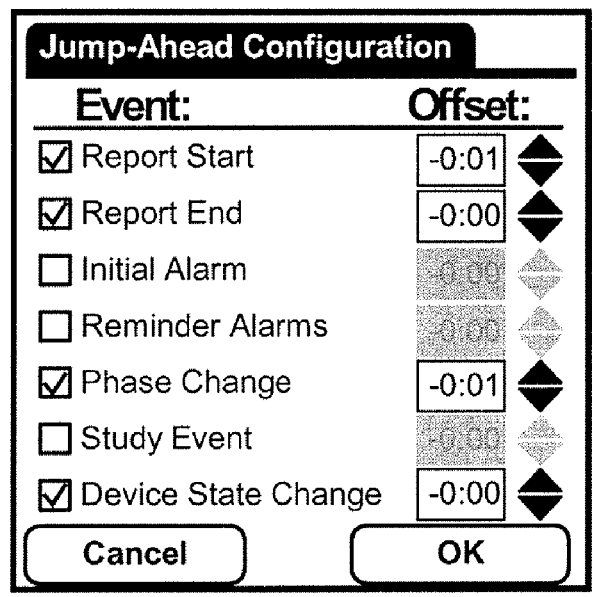
FIG. 20 illustrates a user event filter dialog screen.

These approaches can be combined and extended to support the context and the type of use. For example, the event descriptions offered to the user can range from a complete lack of event details to highly detailed descriptions that include the event identity, date-time, and applicable clinical or operational information. This approach can be extended to a complete graphical representation of the clinical trial schedule in the form of a bar chart, for example as a Gantt chart. Flexibility would range from offering nothing but the next event, to the ability to select from a list of events and to further tailor each event's date-time or opt for an arbitrary user-provided date-time. Additionally, as shown in the filter configuration dialog of FIG. 20, users can be given the ability to choose which events to include and how much to offset the date-time of the location being jumped to from the corresponding scheduled event. This adds an additional layer of customization and automation in the determination of "interesting" events that is based on the vocabulary of scheduled elements and independent variables.

Training Applications

The time shift capability can be used for training purposes. In a clinical investigation, a trainer uses the time shift feature to show the user each of the various scheduled activities and reports within the investigation schedule where the user will need to perform an action. Such scheduled elements include diaries that need to be filled out or questionnaires that need to be answered, or the completion of an epoch and the transition to another epoch. Of particular interest are the first occurrences of each type of report requiring patient input. Using the system, the trainer can jump directly to any element of interest within the schedule, including, for example, the first occurrence of a particular questionnaire or diary. The exact subset of elements depends upon the training context, and the individual(s) being trained. When the trainer uses the system to select the next point to exhibit, the device clock is advanced automatically to the time corresponding to the selected element, and the device then functions as it would if it had reached that point by the passage of real time.

In one typical manner of training, the trainer simply skips over many scheduled events to reach the one of interest. This is complicated if skipped events, such as report completion, are designed to have some effect on a later report or event. In a case where such dependencies exist, a dependency notification component is added to the predictive event determination processor to alert the trainer that a decision point is present, and prompt for the necessary reports or variables to be completed. Alternatively, the dependency notification is enhanced to supply the necessary data automatically. Automatic completion can be performed in such a manner as to successively exercise all branching options at the skipped event.

In a typical scenario, a protocol calls for a week of gathering baseline data. During this time, the subject is instructed to complete daily assessment reports. At the end of the week, the system automatically changes mode and switches to a treatment phase where the subject now has access to medication reports and an enhanced set of assessment reports with a few extra questions added or some questions removed. In this situation, the trainer initially desires to jump from one baseline assessment report to another. Then, the trainer would want to advance to, but not miss, the moment when the device changes modes to show the subject how the display and offerings change in the treatment phase.

The time shift feature is also important for training the clinicians who will manage the conduct of the clinical investigation and care for the human subjects. For example, a protocol may require a clinician to be familiar with the appearance of a scheduled calculation, such as the average symptom score after a week of use, in order to learn how to use the calculation results in managing the patient at the appropriate time. For example, a common situation is to have a medication event followed by an irregular pattern of assessments, each one differing from the next, such as shown in FIG. 4. Since this is a complex timed sequence based on an arbitrary starting point, it would be cumbersome and error prone for the clinician to determine each assessment event without the help of the time shift feature. Using the time shift feature, the clinician is brought reliably to each assessment in turn.

Testing Applications

A testing agent (human or automated) frequently intends to jump to the points of time in the schedule just prior (e.g., 10 seconds) to the point where the next significant change in operation of the device is scheduled to occur. Examples include changes in report availability, changes in active epoch, changes in the execution of alarm events, and changes in scheduled calculations. Since the scheduling of particular actions, such as which report the patient should complete next, is often contingent on the data supplied through report entry, testers can use the time shift feature to exercise the device through the various possible contingent branches quickly to validate the branching conditions. The time shift feature enables the tester to skip static intervals between events by automatically advancing the device's clock. By jumping between events a tester can verify the accuracy of branching algorithms and automatic calculations.

To illustrate the significant time savings possible with time shift, consider the example of an irregular sequence with a variable starting time shown in FIG. 4. To verify proper behavior, a tester needs to repeat the sequence multiple times to verify proper appearance and disappearance of each report despite missed reports, crossing midnight, changing time zones, or a change from standard time to daylight saving time. Likewise a tester would verify proper sounding of each alarm and its reminders, as well as proper non-sounding of alarms and reminders when a report has been completed, despite crossing midnight, changing time zones, or a change from standard time to daylight saving time. To perform these tests manually would require the tester to calculate literally hundreds of time differentials of varying length, and manually enter these times into a time control interface; this prospect is both highly error prone and extremely time-consuming. Time shift replaces both of these burdensome tasks with a command that is easy to use.

A second common and time-consuming testing example involves verifying proper navigation of workflow through a given report or across the entire protocol. This navigation involves branching that can depend on the completion or non-completion of diaries, on specific responses to specific questions, or on the current protocol phase. To verify the proper operation of the device, each of these branching points must be exercised in a variety of combinations. Reaching each branching point can be a time-consuming endeavor as the various branches may be separated by dozens of days or reports. Again, time shift assists the tester by taking the tester to directly to branching points, while maintaining the proper context and history.

In order to ensure the validity of the captured patient data, it is important that the users participating in a clinical investigation do not have access to the time shift feature. Thus, devices with the time shift feature enabled are clearly marked as such, and are confined to clinical sites and generally not handed out to investigation participants to take home. In an alternative embodiment, device 900 is a dual purpose device, having a training mode and a normal mode. In the training mode, a warning screen is displayed before each event, and no data is sent out from the device. Such dual-purpose behavior risks confusing the clinician or subject as to which state the device is in. Thus, the device can include controls to prevent unintentional switching, as well as indicators and/or messages notifying the user which mode is in effect. For example, enabling time shift could require a pass code known only to the clinician, or the time shift feature could automatically disable and revert to the appropriate real time after an interval of time or inactivity in the testing or training mode. Additionally, the user can be informed that time shift is activated by signs such as a flashing warning on each screen, or a notice when completing a report that the data will not be stored or transmitted. Internally, the device's database and state must be securely copied and stored at the time of entering the time shift enabled mode so that the device may be later restored to the proper state when the testing or training mode reverts to normal real time operation.

Other embodiments are within the following claims.

What is claimed is:

1. A health monitoring device comprising:
    a clock, wherein the value of the clock comprises an operating date-time of the health monitoring device as the device executes a health monitoring schedule based on a study definition that defines a planned date-time for scheduled elements and events of interest in the study definition to occur and wherein the clock value determines an operational state of the health monitoring device;
    a data logger module including logic for:
        collecting a first set of health information from a subject or clinician during a first time range and a second set of health information from the subject or clinician during a second time range, at least one of the second set of health information and the second time range being determined in part by a content of the first set of health information, the first and second time ranges being part of the health monitoring schedule;
        recording the first and second sets of health information in a computer readable medium; and
        including a time stamp with the recorded health information in the computer readable medium;
    a user interface for receiving the sets of health information from the subject or the clinician;
    a time shifting module including logic to permit, in a time shifting mode, an adjustment of the clock from a first event of interest in the health monitoring schedule, corresponding to a first operational state of the device, to at or relative to a second event of interest in the health monitoring schedule, corresponding to a second operational state of the device, the device operating at the second event of interest in the health monitoring schedule in the same manner and collecting health information from the subject or clinician in the same manner as if the device had reached the second event of interest without intervention by the time shifting module and resulting in activation of the second operational state of the health monitoring device;
    wherein the time shifting module further includes logic to prevent adjustment of the date and/or time to alter operational state of the health monitoring device and move to the second event of interest when the device is not in the time shifting mode;
    wherein adjustment of the clock from the first point in the health monitoring schedule to the second event of interest in the health monitoring schedule changes an operational state of the device without modification to the study definition; and
    a display having a screen for displaying information corresponding to the operational state of the device.

2. The device of claim 1, wherein the logic for collecting a first set of health information and a second set of health information includes logic to collect diary entries.

3. The device of claim 1, wherein the logic for collecting a first set of health information during a first time range and a second set of health information during a second time range includes logic to determine first and second time ranges that correspond to at least one of a specified time of day, and a period relative to an event.

4. The device of claim 1, wherein the logic to permit an adjustment of the clock includes logic to adjust the operating date-time of the health monitoring device by selecting an event in lieu of specifying an actual time.

5. The device of claim 1, wherein the logic to permit an adjustment of the clock includes logic to set the second event of interest in the health monitoring schedule to a specific point relative to a time range during which the subject or clinician is permitted to enter health information.

6. The device of claim 1, wherein the logic to permit an adjustment of the clock includes logic to set the clock of the health monitoring device to a specific point in a schedule of a medical treatment.

7. The device of claim 1, wherein the logic to permit an adjustment of the clock includes logic to set the second event of interest in the health monitoring schedule to a point in time selected as a result of a calculation based on health information collected prior to the second event of interest in the health monitoring schedule.

8. The device of claim 1, wherein the data logger module includes logic for providing the health monitoring schedule with a plurality of branches, and wherein the device executes one or more of the branches based on health information received from the subject or clinician.

9. The device of claim 1, wherein the logic for collecting a first set of health information and a second set of health information includes logic to collect a diary completed by the subject or clinician.

10. The device of claim 1, wherein the logic for collecting a first set of health information and a second set of health information includes logic to collect a questionnaire completed by the subject or clinician.

11. The device of claim 1, wherein the logic for collecting a first set of health information and a second set of health information includes logic to collect a response of the subject or clinician to a medical event.

12. The device of claim 1, wherein the logic to permit an adjustment of the clock of the health monitoring device to the second event of interest in the health monitoring schedule includes logic for displaying the screen requiring a response from the subject or clinician.

13. The device of claim 12, wherein the logic for displaying the screen requiring a response from the subject or clinician provides a questionnaire for completion by the said subject or clinician.

14. The device of claim 12, wherein the logic for displaying the screen requiring a response from the subject or clinician provides a report for completion by the said subject or clinician.

15. The device of claim 12, wherein the logic for displaying the screen requiring a response from the subject or clinician includes a request for confirmation of a medical event.

16. The device of claim 12, wherein the logic for displaying the screen requiring a response from the subject or clinician provides a request for a subjective response of the said subject or clinician to a medical event.

17. The device of claim 1, wherein the time shifting module further includes logic for selecting the second event of interest for use in training a user of the health monitoring device.

18. The device of claim 1, wherein the time shifting module further includes logic for selecting the second event of interest for use in testing an application of the health monitoring device.

19. The device of claim 1, wherein the logic to permit an adjustment of the clock of the health monitoring device includes logic to permit advancing the operating date-time of the health monitoring device.

20. The device of claim 1, wherein the logic to permit an adjustment of the clock of the health monitoring device includes logic to permit retrogressing the operating date-time of the health monitoring device to an earlier operating date-time of the health monitoring device.

21. The device of claim 1, wherein the time shifting module automatically jumps from the first event of interest to immediately before or at the second event of interest.

22. A method of operating a health monitoring device, the method comprising:
collecting in the health monitoring device a first set of health information from a subject or clinician during a first time range and a second set of health information from the subject or clinician during a second time range, at least one of the second set of health information and the second time range being determined in part by a content of the first set of health information, the first and second time ranges being part of a health monitoring schedule, wherein the health monitoring schedule is based on a study definition;

recording the first and second sets of health information in the health monitoring device;
including a time stamp with the recorded health information; and
initiating a time shifting mode that permits a user of the health monitoring device to adjust an operating date-time of the health monitoring device from a first event of interest in the health monitoring schedule, corresponding to a first operational state of the device, to at or relative to a second event of interest in the health monitoring schedule, corresponding to a second operational state of the device, the health monitoring device operating at the second event of interest in the health monitoring schedule in the same manner and collecting heath information from the subject or clinician in the same manner as if the health monitoring device had reached the second event of interest without intervention by the user and resulting in activation of the second operational state of the health monitoring device,
wherein adjustment of the operating date-time of the health monitoring device from the first event of interest in the health monitoring schedule to the second event of interest in the health monitoring schedule changes an operational state of the device without modification to the study definition.

23. The method of claim 22, wherein collecting the health information includes collecting diary entries.

24. The method of claim 22, wherein collecting in a health monitoring device a first set of health information and a second set of health information includes determining the first and second time ranges that correspond to at least one of a specified time of day, and a period relative to an event.

25. The method of claim 22, wherein initiating a time shifting mode that permits a user of the health monitoring device to adjust the operating date-time of the health monitoring device includes the user adjusting the operating date-time of the health monitoring device by selecting an event in lieu of specifying an actual time.

26. The method of claim 22, wherein initiating a time shifting mode that permits a user of the health monitoring device to adjust the operating date-time of the health monitoring device includes setting the second event of interest in the health monitoring schedule to a specific point relative to a time range during which the subject or clinician is permitted to enter health information.

27. The method of claim 22, wherein initiating a time shifting mode that permits a user of the health monitoring device to adjust the operating date-time of the health monitoring device includes setting the clock of the health monitoring device to a specific point in a schedule of a medical treatment.

28. The method of claim 22, wherein initiating a time shifting mode that permits a user of the health monitoring device to adjust the operating date-time of the health monitoring device includes setting the second event of interest in the health monitoring schedule to a point in time selected as a result of a calculation based on health information collected prior to the second event of interest in the health monitoring schedule.

29. The method of claim 22, wherein operating the health monitoring device comprises providing the health monitoring schedule with a plurality of branches, and wherein the health monitoring schedule executes one or more of the branches based on health information received from the subject or clinician.

30. The method of claim 22, wherein collecting in a health monitoring device a first set of health information and a second set of health information includes logic for collecting at least one of a diary completed by the subject or clinician, a questionnaire completed by the subject or clinician, and a response of the subject or clinician to a medical event.

31. The method of claim 22, wherein initiating a time shifting mode that permits a user of the health monitoring device to adjust the operating date-time of the health monitoring device includes setting the second event of interest in the health monitoring schedule to a time in the health monitoring schedule when the health monitoring application first causes a screen to be displayed that requires a response from the subject or clinician.

32. The method of claim 22, wherein initiating a time shifting mode that permits a user of the data logging application to adjust an operating date-time of the health monitoring device to a second event of interest in the health monitoring schedule includes permitting the user to advance the operating date-time of the health monitoring device.

33. The method of claim 22, wherein initiating a time shifting mode that permits a user of the data logging application to adjust an operating date-time of the health monitoring device to a second event of interest in the health monitoring schedule includes permitting the user to retrogress the operating date-time of the health monitoring device to an earlier operating date-time of the health monitoring device.

34. The method of claim 22, wherein the time shifting mode permits selection of the second event of interest for use in training the user of the data logging application.

35. The method of claim 22, wherein the time shifting mode permits selection of the second event of interest for use in testing the data logging application.

36. The method of claim 22, wherein the time shifting mode automatically jumps from the first event of interest to immediately before or at the second event of interest.

* * * * *